(12) United States Patent
Levine et al.

(10) Patent No.: US 7,031,773 B1
(45) Date of Patent: Apr. 18, 2006

(54) IMPLANTABLE CARDIAC STIMULATION SYSTEM PROVIDING AUTOCAPTURE AND LEAD IMPEDANCE ASSESSMENT AND METHOD

(75) Inventors: Paul A. Levine, Santa Clarita, CA (US); Balakrishnan Shankar, Valencia, CA (US); Kenneth R. McNeil, II, Valencia, CA (US); Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 504 days.

(21) Appl. No.: 10/340,099

(22) Filed: Jan. 10, 2003

(51) Int. Cl.
*A61N 1/362* (2006.01)

(52) U.S. Cl. .................................................. 607/28
(58) Field of Classification Search ............... 607/9–28
See application file for complete search history.

(56) References Cited

U.S. PATENT DOCUMENTS

| | | | | |
|---|---|---|---|---|
| 4,140,131 | A | * | 2/1979 | Dutcher et al. ............... 607/29 |
| 4,686,988 | A | | 8/1987 | Sholder ................ 128/419 PT |
| 4,708,142 | A | | 11/1987 | DeCote, Jr. ........... 128/419 PT |
| 4,729,376 | A | | 3/1988 | DeCote, Jr. ........... 128/419 PT |
| 4,969,467 | A | | 11/1990 | Callaghan et al. .... 128/419 PG |
| 5,003,975 | A | | 4/1991 | Hafelfinger et al. .. 128/419 PG |
| 5,350,410 | A | | 9/1994 | Kleks et al. ................... 607/28 |
| 5,476,485 | A | | 12/1995 | Weinberg et al. ............. 607/28 |
| 5,814,088 | A | | 9/1998 | Paul et al. ...................... 607/28 |
| 5,855,594 | A | | 1/1999 | Olive et al. .................... 607/28 |
| 6,430,441 | B1 | | 8/2002 | Levine .......................... 607/28 |
| 6,546,288 | B1 | * | 4/2003 | Levine .......................... 607/28 |

FOREIGN PATENT DOCUMENTS

| EP | 0 338 363 A2 | 10/1989 |
|---|---|---|
| EP | 0 338 363 A3 | 10/1989 |
| EP | 0 338 363 B1 | 10/1989 |
| EP | 0 338 364 B1 | 10/1989 |
| EP | 0338363 B1 | 10/1989 |
| EP | 0338863 A2 | 10/1989 |
| EP | 0338863 A3 | 10/1989 |

OTHER PUBLICATIONS

Binner, Ludwig et al., "*Autocapture Enhancements: Unipolar and Bipolar Lead Compatibility and Bipolar Pacing Capability on Bipolar Leads*," PACE 2003; 26[Pt. II]):221-224.

Clarke, Malcolm et al., "*Automatic Adjustment of Pacemaker Stimulation Output Correlated with Continuously Monitored Capture Thresholds: A Multicenter Study*," PACE 1998; 21: 1567-1575.

* cited by examiner

*Primary Examiner*—Scott M. Getzow

(57) ABSTRACT

An implantable cardiac stimulation system provides autocapture assessment and lead impedance surveillance. The system includes a pulse generator that provides pacing stimulation pulses and a lead system including a plurality of electrodes that provide a plurality of different electrode configurations. The system further includes a switch that selectively couples the pulse generator to any one of the plurality of pacing electrode configurations and an autocapture circuit that performs autocapture tests with the pulse generator. The autocapture circuit includes a capture detector that detects evoked responses with an evoked response electrode configuration. When there is a failure to detect an evoked response, an impedance measuring circuit measures the lead impedance of the evoked response electrode configuration. If the measured lead impedance is outside of a given range, the switch couples the pulse generator to an electrode configuration other than the evoked response electrode configuration. Thereafter, the autocapture circuit performs a further autocapture and impedance measuring test or sets the pacing output to a level which assures capture.

34 Claims, 4 Drawing Sheets

IMPLANTABLE CARDIAC STIMULATION SYSTEM PROVIDING AUTOCAPTURE AND LEAD IMPEDANCE ASSESSMENT AND METHOD

FIELD OF THE INVENTION

The present invention generally relates to an implantable cardiac stimulation system that provides electrical therapy to a patient's heart. The present invention more particularly relates to such a system that automatically performs autocapture and lead impedance evaluations.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing polarity electrode configurations. In unipolar pacing, the pacing stimulation pulses are applied between a single electrode carried by the load, in electrical contact with the desired heart chamber, and the pulse generator case. The electrode serves as the cathode (negative pole) and the case serves as the anode (positive pole). In bipolar pacing, the pacing stimulation pulses are applied between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

The energies of the applied pacing pulses are selected to be above the pacing energy stimulation threshold of the respective heart chamber to cause the heart muscle of that chamber to depolarize or contract. If an applied pacing pulse has an energy below the pacing energy stimulation threshold of the respective chamber, the pacing pulse will be ineffective in causing the heart muscle of the respective chamber to depolarize or contract. As a result, there will be failure in sustaining the pumping action of the heart. It is therefore necessary to utilize applied pacing pulse energies which are assured of being above the pacing energy stimulation threshold.

However, it is also desirable to employ pacing energies which are not exorbitantly above the stimulation threshold. The reason for this is that pacemakers are implanted devices and rely solely on battery power. Using pacing energies that are too much above the stimulation threshold would result in early depletion of the battery and hence premature device replacement. Prior to autocapture, the capture threshold would be assessed at the periodic follow-up visits with the physician and the output of the pacemaker adjusted (programmed) to a safety margin that was appropriate based on the results of that evaluation. However, capture thresholds may change between scheduled follow-up visits with the physician. A refinement of the technique of periodic capture threshold measurements by the physician was the automatic performance of capture threshold assessment and the automatic adjustment of the output of the pulse generator. Capture threshold may be defined in terms of pulse amplitude, either voltage or current, pulse duration or width, pulse energy, pulse charge or current density. The parameters that can be easily adjusted by the clinician are pulse amplitude and pulse width. With the introduction of autocapture, the implanted pacing system periodically and automatically assesses the capture threshold and then adjusts the delivered output. It also monitors capture on a beat-by-beat basis such that a rise in capture threshold will be recognized allowing the system to compensate by delivery initially of higher-output back-up or safety pulses and then incrementing the output of the primary pulse until stable capture is again demonstrated. The output amplitude of the pacing stimulus is set slightly above the measured capture threshold minimizing battery drain while the patient is protected by the significantly higher output back-up safety pulse. These evaluations are often referred to as autocapture tests or simply autocapture.

As is well known in the art, the stimulation threshold of a heart chamber can, for various reasons, change over time. Hence, pacemakers that incorporate autocapture are generally able to periodically and automatically perform autocapture tests. In this way, the variations or changes in stimulation threshold can be accommodated.

When a pacing pulse is effective in causing depolarization or contraction of the heart muscle, it is referred to as "capture" of the heart. Conversely, when a pacing pulse is ineffective in causing depolarization or contraction of the heart muscle, it is referred to as "lack of capture" or "loss of capture" of the heart.

When a pacemaker performs an autocapture test, its pulse generator applies a succession of primary pacing pulses to the heart at a basic rate. The output of the primary pulse is progressively reduced. In one known system, there will be a minimum of two consecutive pulses at a given energy before the output associated with the primary pulse is reduced or increased. The output of successive primary pacing pulses is reduced by a known amount and capture is verified following each pulse. If a primary pulse results in loss of capture, a backup or safety pulse is applied to sustain heart activity. If there is loss of capture associated with the primary pulse on two successive cycles, this is interpreted as being sub-threshold. At that time, the output is progressively increased in small increments until capture is confirmed on two consecutive primary pulses. This, of course, is but one example. As is known in the art, a single pulse or any number of pulses may be used. The lowest output setting that results in capture on consecutive pulses starting from a low value where there is loss of capture is defined as the capture threshold. The present system then automatically adjusts the output with a working margin of an additional 0.25 Volts. In these methods, capture may be verified by detecting the evoked response associated with the output pulse, the T-waves, mechanical heart contraction, changes in cardiac blood volume impedance, or another signature of a contracting chamber.

Loss of capture can have many different causes. A common causes involves lead failure. Lead failure may result, for example, when the two conductors of a bipolar pacing lead become shorted together. Another lead failure may involve an open circuit where the continuity of one or both conductors in a bipolar lead is disrupted. In the event of either occurrence, switching from a bipolar pacing polarity electrode configuration to a unipolar pacing polarity electrode configuration may restore stimulation effectiveness.

Pacemakers are also capable of sensing. When programmed to the bipolar sensing configuration, the signal that is detected is the voltage difference between the two active electrodes inside the heart. In a unipolar sensing configuration, the signal that is detected is the voltage difference between one electrode in the heart and an electrode located elsewhere. Most commonly, this is the metallic housing of the pulse generator. Unipolar sensing can also be further specified as being between the electrode tip inside the heart and the housing of the pulse generator or between the proximal ring electrode that is set back from the tip and the housing of the pulse generator.

In one implementation of autocapture, the output configuration may be unipolar and the sensing configuration may be bipolar. Further, in the current implementation, autocapture may not be enabled with a dedicated unipolar lead or a bipolar lead programmed to a unipolar sensing configuration.

While autocapture is generally used with ventricular leads, it may be used with atrial leads as well. Hence, it is to be understood that the invention is applicable for either the atrial and/or ventricular leads.

Pacemakers are known having lead supervision wherein lead impedance is measured on either a beat-to-beat or more commonly, periodic basis. If the lead impedance is above or below a certain threshold, the pacing electrode configuration may be automatically switched to a unipolar pacing electrode configuration.

Impedance measurement on a beat-to-beat basis increases the power consumption of the implanted device and consequently reduces the longevity of the device. Assessing lead impedance, also called stimulation impedance, has the same limitations as assessing the capture threshold on a periodic but infrequent basis. Problems may be manifest between scheduled evaluations leaving the patient unprotected if a problem were to develop. Still further, if autocapture were to be enabled, the output configuration is unipolar and impedance measurements would be made in the unipolar configuration. A mechanical problem developing in a lead is likely to be manifest in the bipolar configuration first. As such, an early manifestation of a lead malfunction may not be appreciated in the unipolar output configuration. If a problem were detected, reverting to the unipolar sensing configuration based upon lead impedance may require that autocapture be disabled. The present invention addresses these issues by providing an implantable cardiac stimulation system which conserves energy while providing lead supervision when required, maintaining autocapture, and most importantly, continued stimulation of the heart in the event of a lead failure.

SUMMARY

The present invention provides an implantable cardiac stimulation system that includes autocapture and lead impedance assessment. The system measures lead impedance when there is a failure to detect an evoked response with a given electrode evoked response sensing configuration during autocapture. Should the measured impedance be outside a given range, lead failure is presumed and an electrode configuration other than the given electrode configuration is used for regular pacing. Autocapture is maintained and an autocapture test is performed with the new pacing electrode configuration and regularly thereafter.

Accordingly, the invention provides an implantable cardiac stimulation system that provides autocapture and lead impedance assessment. The system includes a pulse generator that provides pacing stimulation pulses and a lead system including a plurality of electrodes that provide a plurality of different electrode configurations. The system further includes a switch that selectively couples the pulse generator to any one of the plurality of pacing electrode configurations. An autocapture circuit performs autocapture tests with the pulse generator. The autocapture circuit includes a capture detector that detects evoked responses during an autocapture test with the capture detector coupled by the switch to a current one of the plurality of electrode configurations. An impedance measuring circuit measures lead impedance of the current electrode configuration responsive to a failure to detect an evoked response by the capture detector during an autocapture test, and causes the switch to couple the pulse generator to an electrode configuration other than the current one of the plurality of electrode configurations if the measured impedance is outside a predetermined impedance range.

The pulse generator provides a primary pacing pulse and a corresponding backup pacing pulse if there is a failure to detect an evoked response to the primary pacing pulse. The impedance measuring circuit measures the lead impedance during a backup pulse.

The electrode configuration to which the pulse generator is switched is preferably a unipolar pacing electrode configuration. The backup pacing pulse during which lead impedance is measured is a bipolar pacing pulse resulting in a diagnosis of loss of capture causing delivery of an increased output associated with the primary pulse.

The autocapture circuit may perform a further autocapture test after the pulse generator is coupled to the other electrode configuration. The system may further include an alerting mechanism that provides the patient with a perceptible indication when the pulse generator is coupled to the other electrode configuration.

The system may include at least one lead providing a plurality of different atrial electrode configurations and/or at least one lead providing a plurality of different ventricular electrode configurations. The electrode configurations preferably include a bipolar electrode configuration and a unipolar electrode configuration.

The present invention further provides an implantable cardiac stimulation system comprising stimulation means for providing pacing stimulation pulses, lead means including a plurality of electrodes for providing a plurality of different pacing electrode configurations, and switch means for selectively coupling the stimulation means to any one of the plurality of pacing electrode configurations. The system further comprises autocapture means for performing autocapture tests with the stimulation means. The autocapture means includes capture detection means for detecting evoked responses during an autocapture test with the capture detection means coupled by the switch means to a current one of the plurality of electrode configurations and impedance measuring means for measuring lead impedance of the current electrode configuration responsive to a failure to detect an evoked response during an autocapture test and causing the switch means to couple the stimulation means to an electrode configuration other than the current one of the plurality of electrode configurations if the measured impedance is outside a predetermined impedance range. The current electrode configuration may be a bipolar electrode configuration.

The present invention still further provides, in an implantable cardiac stimulation system, a method of providing autocapture and lead impedance assessment. The method includes the steps of applying a primary pacing pulse to a chamber of a patient's heart with a pulse generator coupled to a first one of a plurality of selectable electrode configurations, detecting for an evoked response with a second one of the plurality of selective electrode configurations to the primary pacing pulse, and providing a backup pacing pulse to the chamber of the heart with the pulse generator coupled to the second one of the plurality of selectable electrode configurations upon a failure to detect an evoked response. The method further includes the steps of measuring impedance of the second one of the plurality of selectable electrode configurations responsive to a failure to detect an evoked response, and coupling the pulse generator to an electrode configuration other than the second one of the plurality of selectable electrode configurations if the measured impedance is outside a predetermined range.

BRIEF DESCRIPTION OF THE DRAWINGS

Further features and advantages of the present invention may be more readily understood by reference to the following description taken in conjunction with the accompanying drawings, in which.

DESCRIPTION OF ILLUSTRATIVE EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
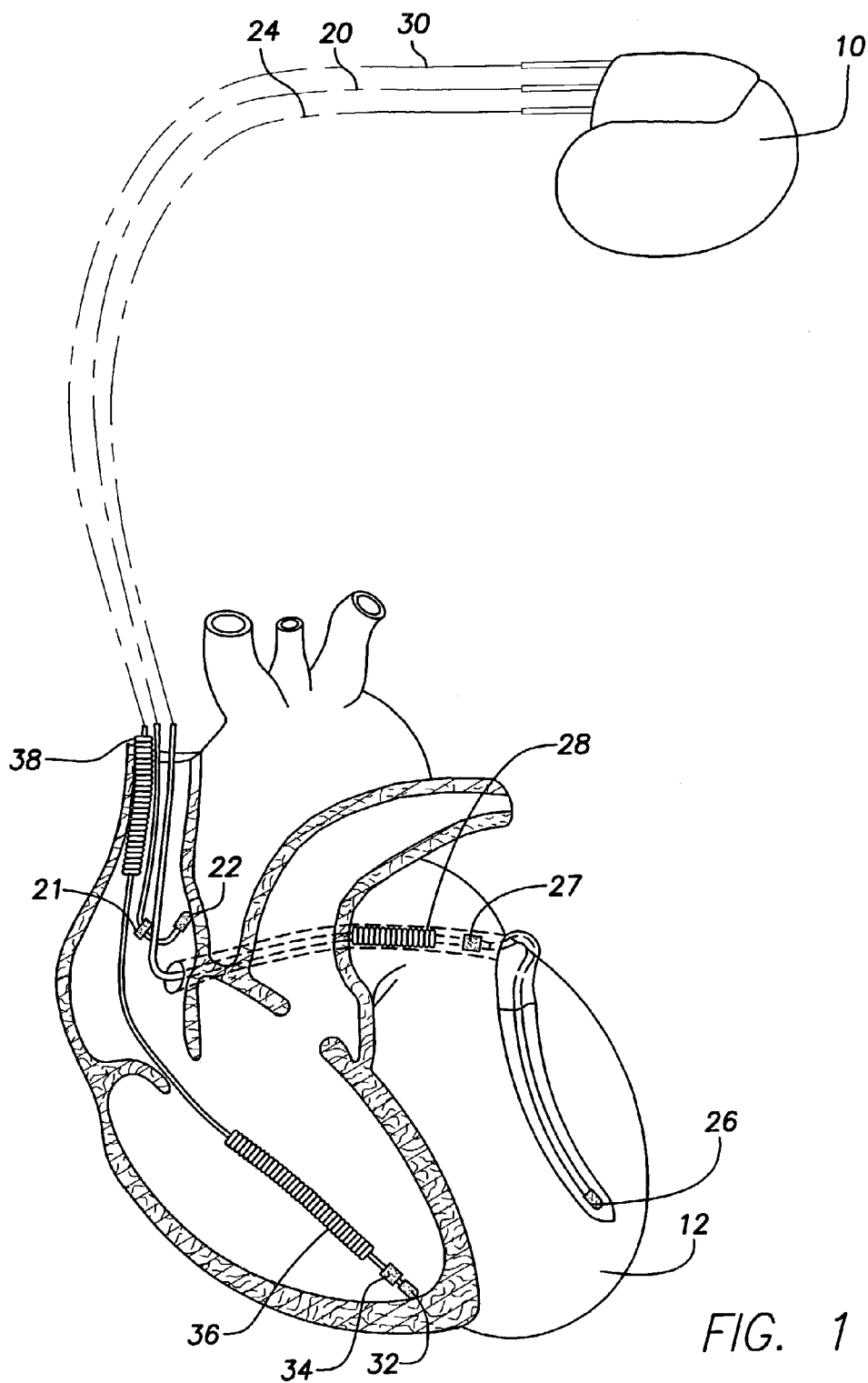
FIG. 1 is a simplified diagram illustrating an implantable cardiac stimulation system embodying the present invention in electrical communication with a patient's heart for delivering multi-chamber stimulation and shock therapy.

As shown in FIG. 1, there is a stimulation system including a device 10 and three leads, 20, 24 and 30, coupling the device to a patient's heart 12 for delivering multi-chamber stimulation and shock therapy. To sense atrial cardiac signals and to provide right atrial chamber stimulation therapy, the stimulation device 10 is coupled to an implantable right atrial lead 20 having an atrial ring electrode 21 and an atrial tip electrode 22, which typically are implanted in the patient's right atrial appendage although can be positioned in any location in the atrium. The electrodes 21 and 22 may be used as a bipolar electrode pair for bipolar pacing of the right atrium. Alternatively, either electrode 21 or electrode 22 (preferably electrode 22) may be used with the case of the device 10 for unipolar pacing of the right atrium.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. For pacing the right ventricle, the electrodes 32 and 34 may be used together for bipolar pacing or alternatively, either electrode 32 or electrode 34 (preferably electrode 32) may be used with the case of the device 10 for unipolar pacing.

Figure 2:
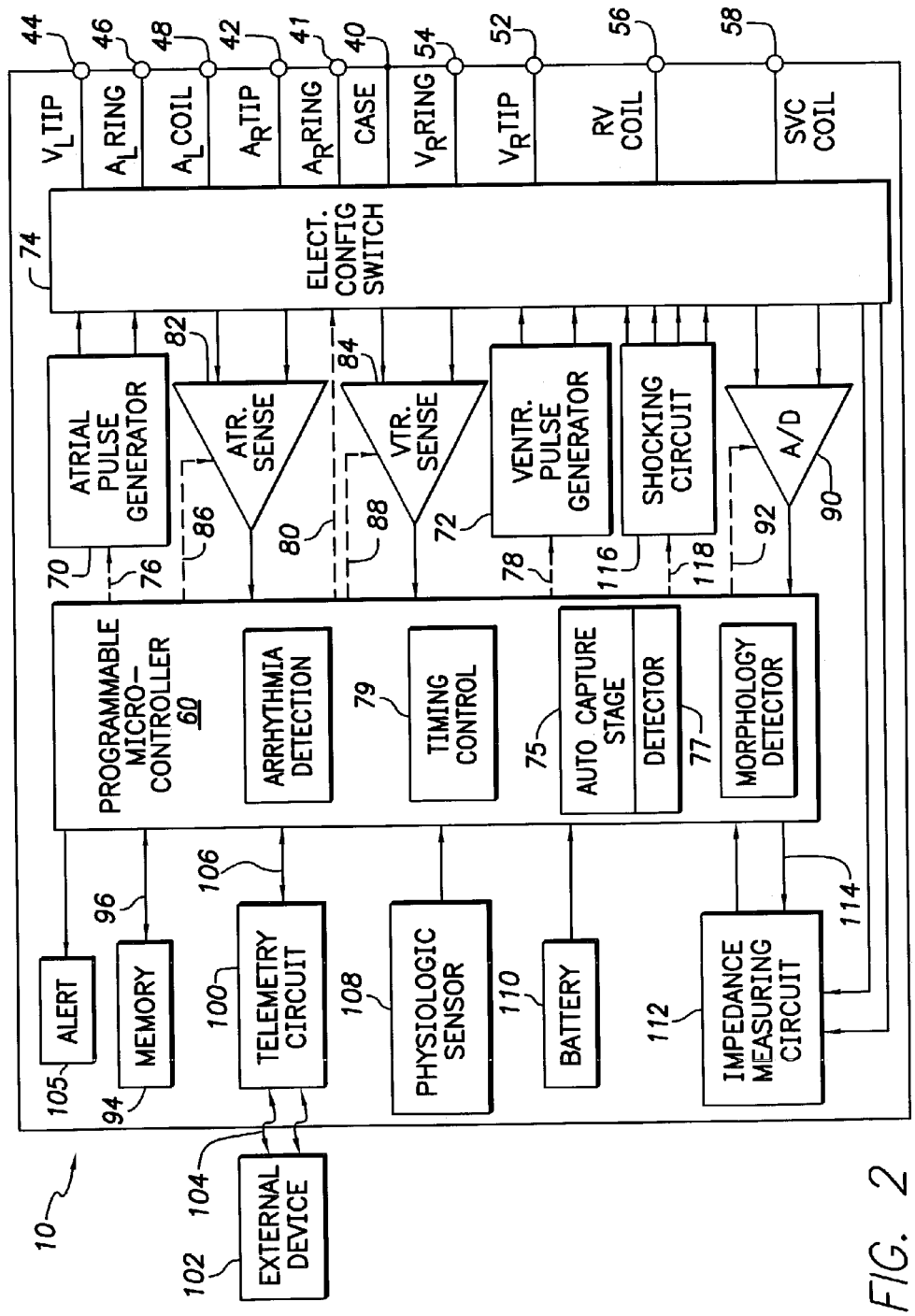
FIG. 2 is a functional block diagram of a multi-chamber implantable stimulation device embodying the present invention illustrating the basic elements thereof for providing cardioversion, defibrillation and pacing stimulation in four chambers of the heart as well as autocapture and lead impedance surveillance in accordance with an embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar"

modes and pacing polarity electrode configurations. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring terminal ($A_R$ RING) 41 adapted for connection to the right atrial ring electrode 21.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, additional elements and functions within the device as they more particularly pertain to this embodiment of the present invention will now be described. The microcontroller includes an autocapture circuit or stage 75. With respect to autocapture, the data acquisition system 90 may be coupled to the microcontroller and include dedicated detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The autocapture 75 includes an evoked response detector 77 that detects a depolarization signal during a window following a stimulation pulse, the presence of which indicates that capture has occurred. The autocapture 75 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window. The evoked response detector 77 processes the data provided by the data acquisition system 90 and, based on the amplitude, determines if an evoked response and hence capture has occurred. Capture detection may occur on a beat-by-beat basis or on a sampled basis. Also, capture detection may be performed for either ventricular or atrial pacing.

In accordance with this embodiment, a capture threshold search is performed on a periodic basis, preferably performed once a day, if the system is stable. A capture threshold search would begin with a small increase in pacing rate if the system were otherwise inhibited or at the functional rate if output stimuli are being delivered and at a desired starting point (either a high energy level or the level at which capture is currently occurring) and decrease the output level until capture is lost. At each output level, the pulse generator provides a primary pacing pulse. If an evoked response (capture) is detected, the energy of the next series of primary pacing pulses is decremented. If an evoked response is not detected (capture lost), the primary pacing pulse is followed, fifty to one-hundred milliseconds thereafter, by a backup pacing pulse at a higher energy to assure capture and contraction of the heart chamber. The system then begins to increase the output associated with the primary pulse. The value at which capture is regained is known as the capture threshold. Thereafter, to complete an autocapture assessment, a working margin is added to the capture threshold.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); U.S. Pat. No. 5,350,410 (Kleks et al.); and U.S. Pat. No. 6,430,441 (Levine), which patents are hereby incorporated herein by reference. The type of capture detection system used is not critical to the present invention.

As further shown in FIG. 2, and in accordance with the present invention, the device 10 includes an impedance measuring circuit 112 which is enabled by the microcontroller 60 via a control signal 114. In accordance with this embodiment of the present invention the impedance measuring circuit is enabled whenever there is a failure to detect an evoked response (presumed loss of capture) during an autocapture assessment. More particularly, the impedance measuring circuit 112 measures the lead impedance of the then current pacing electrode configuration used to provide and during the backup pulse. The impedance measuring circuit 112 is advantageously coupled to the switch 74 so that the impedance of the current pacing electrode configuration may be measured. As will also be seen subsequently, if the measured impedance falls outside of a predetermined or programmable impedance range, as for example less than 200 ohms or greater than 2000 ohms or a variance from the previous measurement by 500 ohms or a percentage of the baseline measurements, indicating a lead failure, the impedance measuring circuit 112, through the microcontroller 60, will cause the switch 74 to switch the pacing electrode configuration to an electrode configuration other than the current pacing electrode configuration as for example, a unipolar pacing electrode configuration. The microcontroller 60 will then cause to autocapture 75 to conduct an autocapture test with the unipolar pacing electrode configuration or sets the pacing output to a level which assures capture. In completing the unipolar capture test, the autocapture 75 provides the working margin and then enables continued pacing in the unipolar pacing electrode configuration. In another embodiment, the microcontroller 60 will increase the output to either a programmable value or the back-up pulse output with the unipolar pacing electrode configuration. In this setting, a repeat autocapture threshold test need not be performed.

Still further, the device 10 includes an alert 105. The alert 105 may be, for example, a vibrating transducer or the like for providing a perceptible indication to the patient when the pacing electrode configuration is switched to the unipolar pacing electrode configuration.

Figure 3:
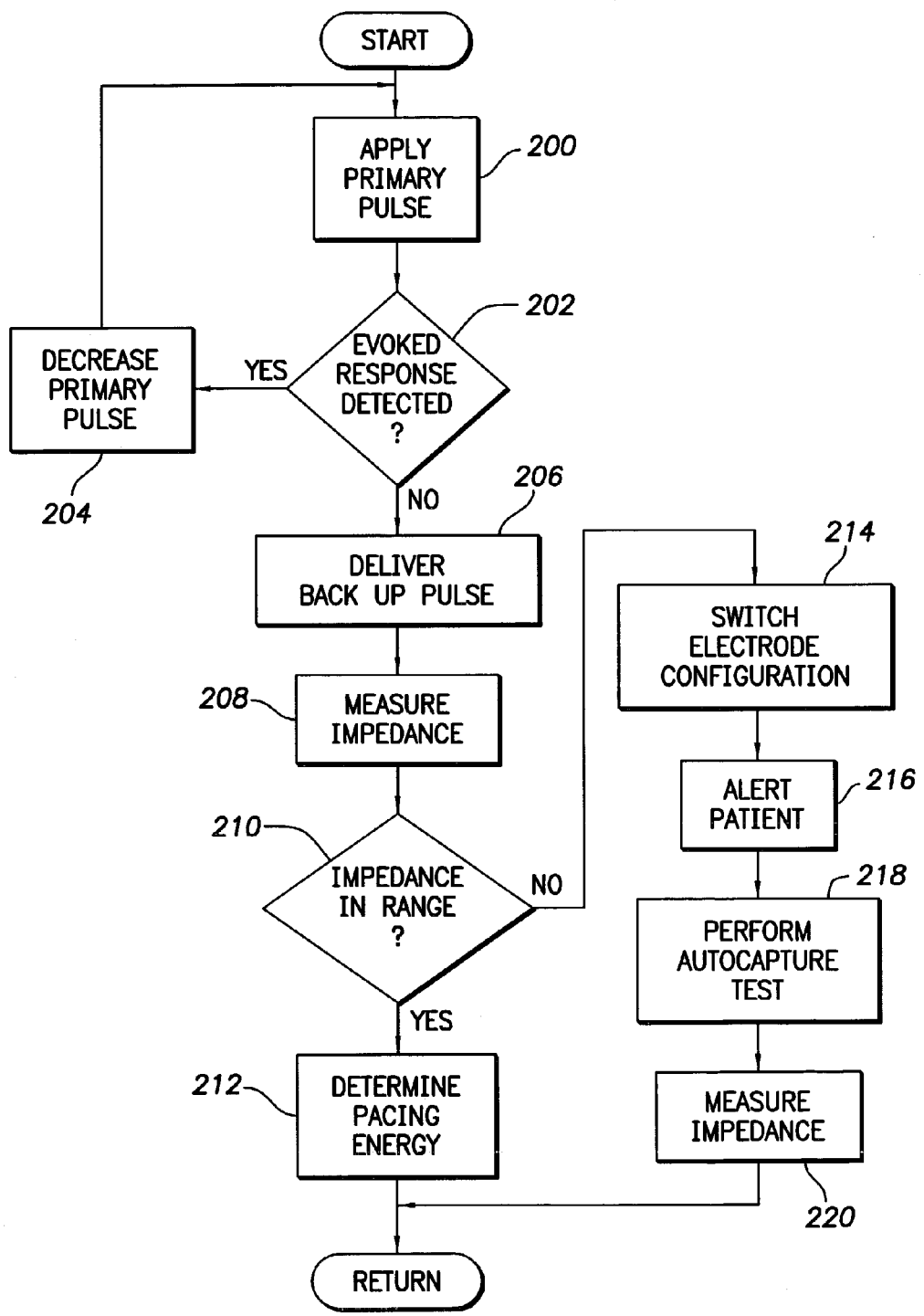
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 begins with an autocapture assessment by the autocapture circuit 75. It is assumed that the heart has been previously paced with a programmed pacing electrode configuration such as a unipolar electrode configuration. It is also assumed that the programmed evoked response sensing electrode configuration has been a bipolar electrode configuration.

The process initiates with an activity block 200 wherein the autocapture circuit 75 causes the pulse generator to provide a primary pacing pulse with the pulse generator coupled to a unipolar electrode configuration. After the primary pacing pulse is applied in accordance with activity block 200, the process proceeds to decision block 202 wherein the autocapture circuit determines if an evoked response to the primary pacing pulse is detected with the bipolar electrode configuration. Failure to detect an evoked response would indicate a possible loss of capture. If there is an evoked response detected, indicating capture, the process advances to activity block 204 wherein the energy of the next primary pacing pulse is decremented and the process then returns back to activity block 200.

If there is a failure to detect an evoked response in accordance with decision block 202, the process advances to activity block 206 wherein the autocapture 75 causes the pulse generator to provide a backup pacing pulse with the pulse generator coupled to the bipolar electrode configuration. The process then immediately advances to activity block 208 wherein, responsive to the failure to detect the evoked response in decision block 202, the impedance measuring circuit 102 is enabled and caused to measure the lead impedance of the bipolar pacing electrode configuration during the backup pulse. The process then advances to decision block 210 wherein it is determined if the measured impedance satisfies one or more predetermined criteria, for example, whether the measured impedance is within a given or predetermined impedance range. The impedance range may be, for example, less than 200 ohms or greater than 200 ohms or a variance from the previous measurement by 500 ohms or some other suitable value.

If the measured impedance is within the given range indicating that there is no lead failure, the process advances to activity block 212 wherein the autocapture assessment is completed by the determination of a final pacing energy. As previously described, the lowest output of the primary pacing pulse that results in restoration of capture is considered to be the capture threshold and to that threshold a working margin is added. Once the effective pacing output has been determined, the process returns.

If in decision block 210 it is determined that the measured impedance of the current or bipolar pacing electrode configuration is outside of the predetermined or given impedance range, the process then advances to activity block 214 wherein the switch 74 is caused to switch the pacing electrode configuration to a different pacing electrode configuration. Preferably, the pacing electrode configuration is switched to a unipolar pacing electrode configuration. Once the pacing electrode configuration is switched in accordance with activity block 214, the process advances to activity block 216 wherein the patient is alerted of the switch in the pacing electrode configuration. Here, the alert 105 is caused to provide a perceptible indication to the patient. This alerts the patient to the need to seek further evaluation allowing the patient's physician to investigate a possible lead failure and then initiate definitive therapy on a permanent basis.

Following the patient alert in accordance with activity block 216, the process then advances to activity block 218 wherein the autocapture 75 performs an autocapture test with the new pacing electrode configuration. When the autocapture 75 completes the autocapture assessment in the new and preferably unipolar pacing and evoked response sensing electrode configuration, the process then advances to activity block 220 wherein the impedance of the new and preferably unipolar electrode configuration is measured. This result may then be logged in memory to document the correction. The process then returns for continued pacing in the unipolar pacing electrode configuration and subsequent regularly occurring autocapture assessment.

Even though an evoked response may not be detected, there still may have been capture. The reason for this is that the primary pacing pulse is applied with one electrode configuration while the evoked response is detected with a different electrode configuration. Since the evoked responses are detected with the normal pacing electrode configuration, the normal pacing electrode configuration is tested if there is a failure to detect an evoked response. A mechanical failure with the normal pacing electrode configuration may thus be detected safely with capture never being lost since a backup pulse is provided upon each failure to detect an evoked response to a primary pulse provided with an electrode configuration other than the evoked response detection electrode configuration.

Figure 4:
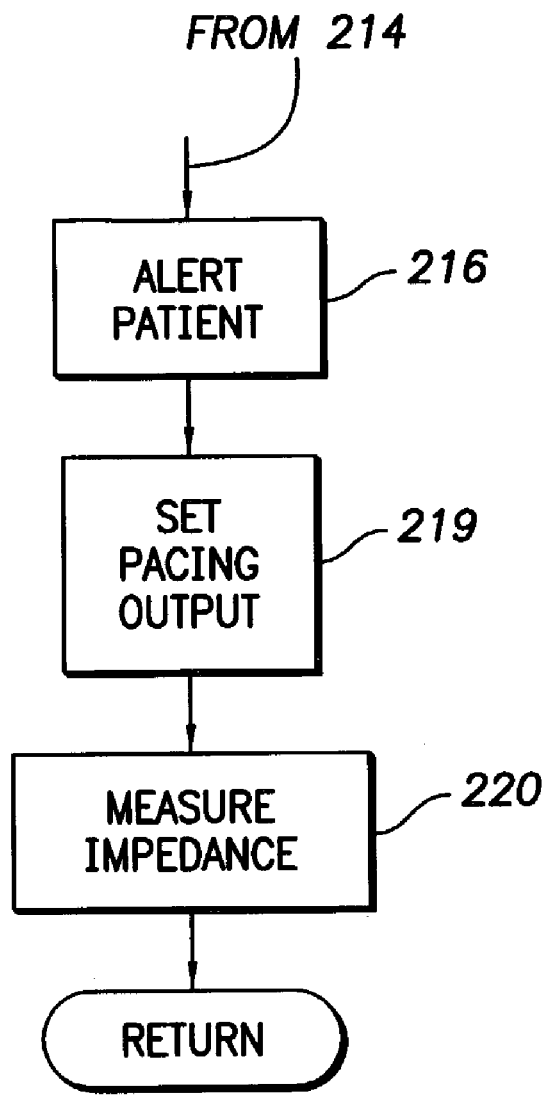
FIG. 4 is a partial flow chart describing an alternative embodiment of the present invention.

FIG. 4 illustrates an alternative embodiment. Here, the process is identical to that shown in FIG. 3 until after the patient alert. Hence, in this implementation, following the patient alert in accordance with activity block 216, the process then advances to activity block 219 wherein the output is increased to a programmable or preset value in the new pacing electrode configuration. The programmable or present value is preferably one which will assure capture. With the pacing output thus set in accordance with activity block 219, the process then advances to activity block 220 wherein the impedance of the new and preferably unipolar electrode configuration is measured. This result may then be logged in memory to document the correction. The process then returns for continued pacing in the unipolar pacing electrode configuration.

While the invention has been described by means of specific embodiments and applications thereof, it is understood that numerous modifications and variations could be made thereto by those skilled in the art without departing from the spirit and scope of the invention. For example, the autocapture assessment and lead impedance surveillance of the present invention may be carried out with pacing electrode configurations for pacing any one of the right atrium, left atrium, right ventricle, or left ventricle. It is therefore to be understood that within the scope of the claims, the invention may be practiced otherwise than as specifically described herein.

What is claimed is:

1. An implantable cardiac stimulation system that provides autocapture and lead impedance assessment comprising:
   a pulse generator that provides pacing stimulation pulses;
   a lead system comprising a plurality of electrodes that provide a plurality of different electrode configurations;
   a switch that selectively couples the pulse generator to any one of the plurality of electrode configurations;
   an autocapture circuit that performs autocapture tests with the pulse generator coupled to a primary pacing electrode configuration, the autocapture circuit comprising a capture detector that detects evoked responses during an autocapture test with the capture detector coupled by the switch to a current one of the plurality of electrode configurations different from the primary pacing electrode configuration; and
   an impedance measuring circuit that measures lead impedance of the current one of the plurality of electrode configurations responsive to a failure in detecting an evoked response by the capture detector during an autocapture test and that causes the switch to couple the pulse generator to an electrode configuration other than the current one of the plurality of electrode configurations if the measured impedance is outside a predetermined impedance range.

2. The system of claim 1 wherein the pulse generator provides a primary pacing pulse and a corresponding back-up pacing pulse if there is a failure to detect an evoked response to the primary pacing pulse and wherein the impedance measuring circuit measures the lead impedance during a back-up pulse.

3. The system of claim 2 wherein the back-up pacing pulse during which lead impedance is measured is provided using the current one of the plurality of electrode configurations.

4. The system of claim 1 wherein the electrode configuration other than the current one of the plurality of electrode configurations is a unipolar electrode configuration.

5. The system of claim 1 wherein the autocapture circuit performs a further autocapture test after the pulse generator is coupled to the electrode configuration other than the current one of the plurality of electrode configurations.

6. The system of claim 1 wherein the impedance measuring circuit performs an impedance measuring test after the pulse generator is coupled to the electrode configuration other than the current one of the plurality of electrode configurations.

7. The system of claim 1 further comprising an alert that alerts the patient when the pulse generator is coupled to the electrode configuration other than the current one of the plurality of electrode configurations.

8. The system of claim 1 wherein the lead system includes at least one lead providing a plurality of different atrial electrode configurations.

9. The system of claim 8 wherein the atrial electrode configurations include a bipolar electrode configuration and a unipolar electrode configuration.

10. The system of claim 1 wherein the lead system includes at least one lead providing a plurality of different ventricular electrode configurations.

11. The system of claim 10 wherein the ventricular electrode configurations include a bipolar pacing electrode configuration and a unipolar pacing electrode configuration.

12. The system of claim 1 wherein the autocapture circuit ceases the autocapture test and sets the pulse generator to a predetermined output level after the pulse generator is coupled to the electrode configuration other than the current one of the plurality of electrode configurations.

13. The system of claim 12 wherein the impedance measuring circuit performs an impedance measuring test after the output of the pulse generator is set to the predetermined level.

14. An implantable cardiac stimulation system that provides autocapture and lead impedance assessment comprising:
   stimulation means for providing pacing stimulation pulses;
   lead means including a plurality of electrodes for providing a plurality of different electrode configurations;
   switch means for selectively coupling the stimulation means to any one of the plurality of electrode configurations;
   autocapture means for performing autocapture tests with the stimulation means coupled to a primary pacing electrode configuration, the autocapture means comprising capture detection means for detecting evoked responses during an autocapture test with the capture detection means coupled by the switch means to a current one of the plurality of electrode configurations different from the primary pacing electrode configuration; and
   impedance measuring means for measuring lead impedance of the current electrode configuration responsive to a failure to detect an evoked response during an autocapture test and causing the switch means to couple the stimulation means to an electrode configuration other than the current one of the plurality of electrode configurations if the measured impedance is outside a predetermined impedance range.

15. The system of claim 14 wherein the stimulation means includes means for providing a primary pacing pulse and a corresponding back-up pacing pulse if there is a failure to detect an evoked response to the primary pacing pulse and wherein the impedance measuring means measures the lead impedance during a back-up pulse.

16. The system of claim 15 wherein the back-up pacing pulse during which lead impedance is measured is provided using the current one of the plurality of electrode configurations.

17. The system of claim 14 wherein the electrode configuration other than the current one of the plurality of electrode configurations is a unipolar electrode configuration.

18. The system of claim 14 wherein the autocapture means performs a further autocapture test after the stimulation means is coupled to the electrode configuration other than the current one of the plurality of electrode configurations.

19. The system of claim 14 wherein the impedance measuring means performs an impedance measuring test after the stimulation means is coupled to the electrode configuration other than the current one of the plurality of electrode configurations.

20. The system of claim 14 further comprising alert means for providing a patient perceptible indication when the stimulation means is coupled to the electrode configuration other than the current one of the plurality of electrode configurations.

21. The system of claim 14 wherein the lead means includes at least one lead providing a plurality of different atrial electrode configurations.

22. The system of claim 21 wherein the atrial electrode configurations include a bipolar pacing electrode configuration and a unipolar pacing electrode configuration.

23. The system of claim 14 wherein the lead means includes at least one lead providing a plurality of different ventricular electrode configurations.

24. The system of claim 23 wherein the ventricular electrode configurations include a bipolar pacing electrode configuration and a unipolar pacing electrode configuration.

25. The system of claim 14 wherein the autocapture circuit means includes means for ceasing the autocapture test and setting the pulse generator to a predetermined output level after the pulse generator is coupled to the electrode configuration other than the current one of the plurality of electrode configurations.

26. The system of claim 25 wherein the impedance measuring means performs an impedance measuring test after the pulse generator is set to the predetermined output level.

27. A method of performing an automatic capture test, the method comprising:
  performing the automatic capture test by applying a plurality of energy-varying pacing pulses to a chamber of a patient's heart using a first electrode configuration selected from a plurality of selectable electrode configurations;
  monitoring for evoked responses to each of the pacing pulses using a second electrode configuration different from the first electrode configuration;
  measuring an impedance value of the second electrode configuration responsive to a failure to detect an evoked response for a given one of the pacing pulses; and
  selecting an electrode configuration other than the second electrode configuration if the measured impedance value does not satisfy one or more predetermined criteria.

28. The method of claim 27 wherein the electrode configuration other than the second electrode configuration is a unipolar electrode configuration.

29. The method of claim 27 further comprising generating a warning signal when the measured impedance value does not satisfy the one or more predetermined criteria.

30. The method of claim 27 wherein the chamber of the heart is an atrium of the heart.

31. The method of claim 27 wherein the plurality of selectable electrode configurations includes a bipolar electrode configuration and a unipolar electrode configuration.

32. The method of claim 27 further comprising adjusting an energy level of the pacing pulses when the measured impedance value does not satisfy the one or more predetermined criterion.

33. An implantable cardiac stimulation system comprising:
  a pulse generator providing primary pacing pulses and back-up pacing pulses;
  a lead system providing a first electrode configuration and a second electrode configuration;
  an autocapture circuit that, responsive to a primary pacing pulse provided using the first electrode configuration, detects an evoked response using the second electrode configuration and that, responsive to a failure to detect an evoked response, causes the pulse generator to provide a back-up pacing pulse; and
  an impedance measuring circuit that measures lead impedance during a back-up pacing pulse.

34. The system of claim 33 wherein the back-up pacing pulse is provided using the second electrode configuration.

* * * * *